United States Patent [19]

Harris et al.

[11] Patent Number: 5,068,384

[45] Date of Patent: Nov. 26, 1991

[54] PHOSPHATE SALTS OF AB-POLYBENZOXAZOLE MONOMER

[75] Inventors: William J. Harris; Zenon Lysenko, both of Midland; Carl W. Hurtig, Saginaw, all of Mich.

[73] Assignee: The Dow Chemical, Midland, Mich.

[21] Appl. No.: 546,596

[22] Filed: Jun. 29, 1990

Related U.S. Application Data

[62] Division of Ser. No. 380,567, Jul. 14, 1989, Pat. No. 4,959,492.

[51] Int. Cl.$^5$ .......................................... C07C 227/04
[52] U.S. Cl. ................................................ 562/453
[58] Field of Search ........................................ 562/453

[56] References Cited

U.S. PATENT DOCUMENTS 3,929,864 12/1975 Papenfuss ............................ 560/23
4,835,306 5/1989 Lysenko ............................... 562/453

OTHER PUBLICATIONS

Iwakura et al., Chem Abst., vol. 68, #13589C (1968).

Primary Examiner—James H. Reamer

[57] ABSTRACT

AB-polybenzoxazole monomer, such as 3-amino-4-hydroxybenzoic acid, can be synthesized in high yields from a hydroxy-benzoic acid or related compound in a three-step process of (1) nitration, (2) hydrolysis of the ester, and (3) reduction of the nitro moiety. The monomer is conveniently recovered as a phosphate salt in high purity by precipitating and recrystallizing from a phosphoric acid solution.

10 Claims, No Drawings

PHOSPHATE SALTS OF AB-POLYBENZOXAZOLE MONOMER

CROSS-REFERENCE TO RELATED APPLICATION

This application is a divisional application of copending application Ser. No. 380,567, filed July 14, 1989, now U.S. Pat. No. 4,959,492.

BACKGROUND OF THE INVENTION

The present invention relates to AB-polybenzoxazole (AB-PBO) monomers and processes for synthesizing them.

AB-polybenzoxazole monomers comprise:

(1) an aromatic group:

(2) an o-amino-hydroxy moiety bonded to said aromatic group, which consists of a primary amine group bonded to said aromatic group and a hydroxy group bonded to said aromatic group in a position ortho to said primary amine group: and (3) an electron-deficient carbon group linked to said aromatic group.

AB-polybenzoxazole monomers preferably conform with formula I:

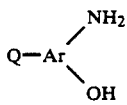
I wherein Q is an electron-deficient carbon group: Ar is an aromatic group: and the amine and hydroxy groups are in ortho position with respect to each other.

The monomer is polymerized by polycondensation in a non-oxidizing solvent acid, such as methanesulfonic acid or polyphosphoric acid, at elevated temperatures, as described in Sybert et al., *Liquid Crystalline Polymer Compositions, Process and Products*, U.S. Pat. No. 4,772,678 (Sept. 20, 1988): Wolfe et al., *Liquid Crystalline Polymer Compositions, Process and Products*, U.S. Pat. No. 4,703,103 (Oct. 27, 1987); Wolfe et al., *Liquid Crystalline Polymer Compositions, Process and Products*, U.S. Pat. No. 4,533,692 (Aug. 6, 1985); Wolfe et al., *Liquid Crystalline Poly(2,6-Benzothiazole) Compositions, Process and Products*, U.S. Pat. No. 4,533,724 (Aug. 6, 1985); Wolfe, *Liquid Crystalline Polymer Compositions, Process and Products*, U.S. Pat. No. 4,533,693 (Aug. 6, 1985): Evers, *Thermoxidatively Stable Articulated p-Benzobisoxazole and p-Benzobisthiazole Polymers*, U.S. Pat. No. 4,359,567 (Nov. 16, 1982); Tsai et al., *Method for Making Heterocyclic Block Copolymer*, U.S. Pat. No. 4,578,432 (Mar. 25, 1986) and 11 Ency. Poly. Sci. & Eng., *Polybenzothiazoles and Polybenzoxazoles*, 601 (J. Wiley & Sons 1988).

The resulting polymers comprise a plurality of mer units which each contain:

(1) an aromatic group: and (2) an oxazole ring fused to said aromatic group and linked at the 2-carbon to an aromatic group in an adjacent mer unit The polymers preferably comprise a moiety which conforms to formula II

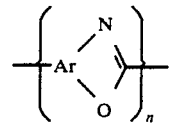
II wherein n is a number of repeating units in excess of one.

The o-amino-hydroxy moiety of the AB-PBO monomer is extremely sensitive to air oxidation as a free base, so the monomer is ordinarily stored as an acid salt of hydrogen chloride. The release of hydrogen chloride gas during polymerization causes foaming of the polymerization mixture which can interfere with the reaction. Typically, the monomer is dehydrohalogenated at moderate temperatures and, optionally, reduced pressure, in a solution of polyphosphoric acid having low viscosity, and then phosphorus pentoxide is added to the solution before polymerizing to high molecular weight, as described in U.S. Pat. No. 4,533,693 which is previously incorporated by reference. The dehydrohalogenation step requires time and requires that equipment be made of materials which are inert with respect to hydrogen halide gases. What is needed is a monomer which does not require a dehydrohalogenation step.

The condensation of AB-PBO is a polycondensation reaction. In such a reaction, the purity of the resulting monomer is critical, because impurities containing only one reactive group act as chain-terminating agents which hold down the molecular weight of the resulting polymer. What is needed is a high yield process to synthesize AB-PBO monomer having a high purity.

SUMMARY OF THE INVENTION

One aspect of the present invention is a process for synthesizing an AB-PBO monomer, said process comprising the steps of:

(1) contacting a hydroxy-ester compound comprising:

(a) an aromatic group;

(b) a hydroxy group bonded to said aromatic group: and (c) an ester moiety having a carboxylate moiety linked to said aromatic group with a nitrating agent under conditions such that the aromatic group is nitrated in a position ortho to the hydroxy group, in an organic solvent, which is inert with respect to all reagents under reaction conditions:

(2) converting the nitrated hydroxy-ester of step (1) to a water-soluble nitrated hydroxy-benzoate salt and dissolving said water-soluble salt in an aqueous solvent; and (3) contacting the water-soluble salt product of step (2) with a hydrogenating agent in the presence of a transition-metal-containing hydrogenation catalyst in an aqueous solution under conditions such that the nitrate group of said water-soluble salt is hydrogenated to form an amine group.

A second aspect of the present invention is a purified salt comprising AB-PBO monomer ions and phosphate ions wherein at least 99 percent of the organic content of the salt is AB-PBO monomer ions.

Processes of the present invention can be used to synthesize monomer salts of the present invention. Monomer salts can be polymerized in solvent acids such as polyphosphoric acid to form AB-PBO polymers without a dehydrohalogenation step. AB-PBO polymers can be coagulated from acid dopes to form high strength fibers, films and other shaped articles.

DETAILED DESCRIPTION OF THE INVENTION

The following terms are used in this application and are defined here for convenience.

AA-Monomer—A monomer suitable for synthesizing polybenzazole polymers, comprising two electron-deficient carbon groups linked by a divalent organic moiety (DM) which is inert with respect to all reagents under polybenzazole polymerization conditions. The electron-deficient carbon groups have the definition and preferred embodiments given herein. The divalent organic moiety is preferably alkyl or an aromatic group, as herein defined, is more preferably an aromatic group, and is most preferably a six-membered aromatic group. Examples of suitable AA-monomers and references to their synthesis are provided in U.S. Pat. No. 4,533,693 at columns 25-32, Tables 4-6, which is incorporated herein by reference. Preferred examples of AA-monomers include terephthalic acid, isophthalic acid, bis-(4-benzoic) acid and oxy-bis-(4-benzoic acid) and acid halides thereof.

AB-Monomer—A monomer suitable for synthesizing polybenzazole polymers, comprising an aromatic group, an o-amino-basic moiety bonded to the aromatic group, and an electron-deficient carbon group bonded to the aromatic group. The aromatic group, the electron-deficient carbon group and the o-amino-basic moiety have the definitions and preferred embodiments given herein. Examples of suitable AB-monomers and processes for their synthesis are provided in U.S. Pat. No. 4,533,693 at columns 33-35, Tables 7-8, which is incorporated herein by reference. Preferred examples of AB-monomers include 3-amino-4-hydroxybenzoic acid, 3-hydroxy-4-aminobenzoic acid, 3-mercapto-4-aminobenzoic acid and the acid halides thereof. AB-monomers are frequently stored as salts of hydrogen chloride or phosphoric acid, because the free-base of the monomer is unstable susceptible to air oxidation.

Aromatic group (Ar)—any aromatic ring or ring system which can be part of a PBZ polymer. Each aromatic group may individually be heterocyclic, but each is preferably carbocyclic and more preferably hydrocarbyl. If an aromatic group is heterocyclic, it is preferably a nitrogen-containing heterocycle.

Each aromatic group may comprise a single aromatic ring, a fused ring system, or an unfused ring system, containing two aromatic moieties linked by a bond or a divalent linking moiety which is inert with respect to PBZ polymerization reagents under PBZ polymerization conditions. If the aromatic group comprises a divalent linking moiety, that moiety preferably comprises an ether linking moiety, a thioether linking moiety, a sulfonyl linking moiety, an alkyl linking moiety, or a halogenated alkyl linking moiety or known equivalents. The divalent linking moiety preferably comprises no more than about 6 carbon atoms. Aromatic groups preferably consist essentially of a single ring.

Size of the aromatic group is not critical as long as the aromatic group is not so big that it prevents further reactions of the moiety in which it is incorporated. Each aromatic group preferably independently comprises no more than about 18 carbon atoms, more preferably no more than about 12 carbon atoms and most preferably no more than about 6 carbon atoms, excluding any divalent linking group and any organic substituent on the aromatic group.

Each aromatic group may independently have substituents which are stable in solvent acid and which do not interfere with the polymerization of monomers for PBZ synthesis, such as halogen atoms, alkoxy moieties, aryloxy moieties or alkyl moieties. Substituents which comprise organic moieties preferably comprise no more than about 12 carbon atoms, more preferably no more than about 6 carbon atoms. Each aromatic group preferably has no substituents other than those specified hereinafter.

Azole ring—an oxazole, thiazole or imidazole ring The carbon atom bonded to both the nitrogen atom and the oxygen, sulfur or second nitrogen atom is the 2-carbon, as depicted in formula III

wherein Z is —O—, —S— or —NR—; and R is hydrogen, an aromatic group, an aliphatic group or an aliphatic-aromatic group, preferably hydrogen or an alkyl group, and most preferably hydrogen. R preferably comprises no more than about 6 carbon atoms, more preferably no more than about 4 and most preferably no more than about 1. Each azole ring is independently preferably oxazole or thiazole and more preferably oxazole. In PBZ polymer, the 4 and 5 carbon atoms are ordinarily fused with an aromatic group.

Azole-forming moiety—an "o-amino-basic moiety" or "electron-deficient carbon group," as those terms are hereinafter defined.

o-Amino-basic moiety—a moiety bonded to an aromatic group, which o-amino-basic moiety contains (1) a first primary amine group bonded to the aromatic group and (2) a hydroxy, thiol or primary or secondary amine group bonded to the aromatic group ortho to said primary amine group.

It preferably comprises a hydroxy, thio or primary amine moiety, more preferably comprises a hydroxy or thiol moiety, and most preferably comprises a hydroxy moiety. If the o-amino-basic moiety comprises two amine groups, preferably both are primary amine groups. If the o-amino-basic moiety contains a secondary amine group, the secondary amine group may comprise an aromatic or an aliphatic group but preferably comprises an alkyl group. The secondary amine group preferably comprises no more than about 6 carbon atoms, more preferably no more than about 4 carbon atoms and most preferably no more than about 1 carbon atom.

BB-Monomer—A monomer suitable for synthesizing polybenzazole polymers, comprising an aromatic group and two o-amino-basic moieties which are bonded to the aromatic group. The aromatic group and the o-amino-basic moieties have the definitions and preferred embodiments given herein. Examples of suitable BB-monomers and processes for synthesis are provided in U.S. Pat. No. 4,533,693 at columns 19-24, Tables 1-3, which is incorporated herein by reference. Examples of preferred BB-monomers include 4,6-diaminoresorcinol, 2,5-diaminohydroquinone and 1,4-dithio-2,5-diaminobenzene. BB-monomers are frequently stored as salts of hydrogen chloride or phosphoric acid, because the free base of the monomer is susceptible to air oxidation.

Electron-deficient carbon group (Q)—any group containing a carbon atom which can react in the solvent acid with an o-amino-basic moiety to form an azole ring, such as the groups listed in column 24, lines 59–66 of the U.S. Pat. No. 4,533,693, which is incorporated herein by reference, and such as an orthoester group, an amidate ester group, a trihalomethyl group or an alkali or alkaline-earth metal carboxylate group. Each electron-deficient carbon group is preferably independently a carboxylic acid or acid halide group and more preferably a carboxylic acid group. Halogens in electron-deficient carbon groups are preferably independently chlorine, bromine or fluorine and are more preferably chlorine.

Solvent acid—a non-oxidizing liquid acid capable of dissolving PBZ polymers, such as sulfuric acid, methanesulfonic acid, polyphosphoric acid and mixtures thereof. The solvent acid highly preferably either is a dehydrating acid or contains a dehydrating agent such as $P_2O_5$. Examples of preferred solvent acids include polyphosphoric acid and mixtures of methanesulfonic acid and phosphorus pentoxide. Polyphosphoric acid preferably has a $P_2O_5$ content by weight of at least about 70 percent, more preferably at least about 75 percent and preferably has a $P_2O_5$ content of at most about 90 percent, more preferably at most about 85 percent. The ratio of methanesulfonic acid to phosphorus pentoxide in mixtures of those compounds is preferably no more than about 20:1 by weight and no less than about 5:1 by weight. The most preferred solvent acid is polyphosphoric acid.

Synthesis of AB-PBO Monomer

AB-PBO monomer is preferably synthesized in a three-step process. The first step is the nitration of a hydroxy-ester compound, which contains:

(1) an aromatic group;

(2) a hydroxy group bonded to said aromatic group; and (3) an ester group having a carboxylate ion linked to said aromatic group.

The aromatic group has the description and preferred embodiments previously given. The carboxylate ion may be linked to the aromatic group by an aliphatic moiety, but is preferably bonded directly to the aromatic group. The hydroxy moiety is preferably not ortho to the carboxylate ester. It is more preferably para to the carboxylate ester. Examples of suitable hydroxy-ester compounds include the methyl to hexyl esters of 4-hydroxybenzoate, 3-hydroxybenzoate, 4-(p-hydroxyphenyl)benzoate and 4-(p-hydroxyphenoxy)benzoate. The most preferred hydroxy-ester compound is a 4-hydroxybenzoate ester.

Some suitable hydroxy-ester compounds, such as methyl 4-hydroxybenzoate, are commercially available. Other suitable esters can be synthesized by known reactions such as esterification of an appropriate hydroxy-benzoic acid of transesterification of an appropriate hydroxy-benzoate ester. Suitable hydroxy-benzoic acids and related compounds can be synthesized by obvious variations of known syntheses, such as those described in B. S. Furniss, *Vogel's Practical Organic Chemistry*— 4th ed. 832 (Longman 1978): A. H. Blatt et al., 2 *Organic Syntheses* 343 (J. Wiley & Sons 1943); and Fieser, 58 *J. Am. Chem. Soc.* 1738 (1936), which are incorporated herein by reference.

The hydroxy-ester compound is contacted with a nitrating agent. The nitration of aromatic compounds is a well-known reaction. The conditions are familiar to persons of ordinary skill in the art, and are reported in numerous references, such as G. M. Loudon, *Organic Chemistry* 590, 598, 1283–86 (Addison-Wesley Publishing Co. 1984), which is incorporated herein by reference. The nitrating agent is preferably nitric acid. The nitric acid is preferably concentrated, such as about 70 to 71 percent nitric acid. The contact is made in a solvent capable of dissolving the hydroxy-ester compound. The solvent is preferably a halogenated aliphatic compound and is more preferably methylene chloride. The solvent must be inert with respect to nitration and with respect to all reagents under reaction conditions. The contact is made in the presence of a catalytic amount of strong acid, such as sulfuric acid. The temperature is preferably no more than about 25° C., more preferably no more than about 15° C. and most preferably no more than about 5° C. It is preferably no less than about $-15°$ C., more preferably no less than about $-10°$ C. and most preferably no less than about $-5°$ C.

The nitration product comprises all of the elements of the hydroxy-ester compound, and further comprises a nitro group bonded to the aromatic group ortho to the hydroxy group. When the hydroxy group is para to the ester moiety, then the nitro groups are primarily all ortho to the hydroxy group. When the hydroxy group is in another position, the product may comprise a mixture of isomers which are separated by known techniques, such as recrystallization.

In the second step, the nitrated hydroxy-ester is converted to a water-soluble salt and dissolved in an aqueous solvent. The nitrated hydroxy-ester is preferably extracted into an aqueous solution by contact with an aqueous solvent and with a base which is in sufficient quantities and is selected such that the nitrated hydroxy-ester is converted into a nitrated hydroxy-benzoate salt which is soluble in water. The base is preferably an alkali or alkaline-earth metal hydroxide. The base is more preferably an alkali metal hydroxide, such as lithium, sodium or potassium hydroxide, and is most preferably sodium hydroxide. The base is preferably dissolved in the aqueous solvent. The resulting water-soluble salt is preferably formed in yields of at least about 90 percent, more preferably at least about 95 percent and most preferably at least about 99 percent, based upon the initial amount of hydroxy-ester compound. The aqueous solution can be used without for the third step purification or isolation.

In the third step of the synthesis, the product from the second step is contacted with a hydrogenating agent in the presence of a catalytic amount of transition-metal catalyst in an aqueous solution under conditions such that the nitro group is hydrogenated and an AB-PBO monomer is formed. Reaction conditions for catalytic hydrogenation of nitro groups are well-known and are described in many standard texts, such as G.M. Loudon, *Organic Chemistry* 1197–98 (Addison-Wesley Publishing Co. 1984), which is incorporated herein by reference.

The contact occurs in an aqueous solution, which is preferably the solution produced in the extraction step. The hydrogenating agent is preferably molecular hydrogen. The catalyst is preferably a noble metal catalyst, such as platinum or palladium. It is more preferably a palladium catalyst. The catalyst is preferably supported and more preferably supported on car
bon. Examples of suitable catalyst include 5-10 weight percent palladium-on-carbon. The reaction takes place in the presence of hydrogen. Of course, oxidizing gases such as oxygen must be excluded from the system. The temperature of the reaction is preferably at least about 30° C., more preferably at least about 20° C. and most preferably at least about 45° C. It is preferably at most about 110° C., more preferably at most about 95° C. and most preferably at most about 65° C.

The product of the hydrogenation step is an AB-PBO monomer in which the electron-deficient carbon group is a carboxylate salt. The positions of the amine, hydroxy and carboxylate groups in the monomer are determined by the position which they and their precursors held in the intermediates used to make the monomer. The monomer is dissolved in an aqueous solution, and is highly susceptible to air oxidation in its free-base state.

The AB-PBO monomer may be precipitated from the aqueous solution by contacting it with a non-oxidizing protic acid to convert the carboxylate salt moiety into a carboxylic acid moiety. The non-oxidizing protic acid is preferably chosen and in sufficient quantities to protonate the o-amino-hydroxy moiety of the monomer, in order to stabilize the monomer against air oxidation. The non-oxidizing protic acid is preferably a hydrogen halide or phosphoric acid, more preferably hydrochloric acid or phosphoric acid, and most preferably phosphoric acid. The monomer precipitates as an acid salt of the non-oxidizing protic acid. The monomer should not be exposed to air or other oxidizing media until it has been contacted with an acid to protonate the o-amino-hydroxy moiety.

The precipitated AB-PBO monomer phosphate salt can be purified by recrystallization from an aqueous phosphoric acid solution. The solution may contain a small amount of reducing agent, such as tin (II) chloride, to reduce any oxidized impurities in the monomer. The solution is heated to any temperature sufficient to cause essentially all of the monomer phosphate salt to dissolve. The temperature is preferably at least about 80° C., more preferably at least about 90° C. and most preferably greater than 100° C. The solution is then cooled to a temperature sufficient to precipitate a substantial portion of monomer phosphate. The temperature is preferably at most about 10° C., more preferably at most about 5° C. and most preferably at most about 0° C.

The recrystallized monomer is preferably washed with a volatile organic non-solvent which forms an azeo-trope with water. The non-solvent is preferably an alcohol having from 1 to 6 carbon atoms, and is more preferably ethanol. The monomer is preferably dried to remove essentially all water and free phosphoric acid.

The processes described above preferably produce at least about 75 percent yield of AB-PBO monomer based upon the beginning hydroxy-ester compound, and more preferably produce at least about 80 percent yield. The purity of AB-PBO monomer phosphate salt, as a weight percentage of the organic content which is AB-PBO monomer ion, is preferably at least about 99 percent, more preferably at least about 99.5 percent and most preferably at least about 99.9 percent by weight.

The AB-PBO monomer phosphate salt comprises ions of AB-PBO monomer and phosphoric acid. The AB-PBO monomer has the description previously given. The aromatic group has the description and preferred embodiments of the aromatic group in the initial hydroxy-ester compound. The electron-deficient carbon group has the meaning and preferred embodiments previously given. It is most preferably carboxylic acid. The electron-deficient carbon group is preferably para to the amine moiety or the hydroxy moiety, and most preferably to the hydroxy moiety. The AB-PBO monomer ion is most preferably an ion of 3-amino-4-hydroxybenzoic acid.

The phosphate ion may, in some cases, be a condensed phosphate, such as pyrophosphate, but is preferably a single phosphate. A single phosphate ion may have two or three AB-PBO monomer ions associated with it, but the average number of phosphate ions associated with each AB-PBO ion is preferably about 1:1.

AB-PBO monomer phosphate ions of the present invention may be polymerized in non-oxidizing solvent acid according to known processes. The solvent acid is preferably polyphosphoric acid containing at least 80 percent $P_2O_5$. When the electron-deficient carbon group does not contain halogen, no dehydrohalogenation step is necessary. Preferred conditions are the polymerization conditions discussed in U.S. Pat. Nos. 4,772,678; 4,703,103; 4,533,692; 4,533,724; 4,533,693; 4,359,567; and 4,578,432 and 11 Ency. Poly. Sci. & Eng., supra. 601, which are previously incorporated herein by reference. The temperature is preferably started at no higher than about 60° C., and raised periodically throughout the reaction. The maximum temperature during the reaction is preferably at least about 70° C., more preferably at least about 100° C, more highly preferably at least about 150° C. and most preferably at least about 190° C. The maximum temperature must be less than the decomposition point of reagents and products, and is preferably at most about 230° C., more preferably at most about 210° C. The reaction should be carried out under a non-oxidizing atmosphere and with vigorous agitation. Other conditions may be found in other literature references.

AB-PBO polymer produced by this process preferably has a molecular weight corresponding to an inherent viscosity in methanesulfonic acid at 25° C. and about 0.05 g/dL of at least about 7 dL/g, more preferably at least about 10 dL/g, more highly preferably at least about 12 dL/g and most preferably at least about 14 dL/g. AB-PBO monomer phosphate salts may also be used in other manner known for hydrochloride salts, such as by polymerizing with AA- and BB-PBZ monomers to form random or block copolymers or by polymerizing with AB-PBT or -PBI monomers to form random copolymers.

AB-PBO polymers can be extruded into fibers and films useful for making composites and laminates according to the processes described in 11 Ency. Poly. Sci & Eng., supra, at 625-31, which is incorporated herein by reference.

WORKING EXAMPLES

The following examples are for illustrative purposes only and are not intended to limit the scope of either the specification or the claims. All parts and percentages are by weight unless otherwise stated.

EXAMPLE 1

Synthesis and Precipitation of AB-PBO Monomer Phosphate Salt

A 152.0 -g (1.0 mole) quantity of methyl 4-hydroxybenzoate is dissolved in one liter of dichloromethane. The solution is cooled to 0° C. and 100 ml of 98 percent sulfuric acid is added. With vigorous stirring 80 ml of 71 percent nitric acid is added dropwise such that the temperature of the mixture does not exceed 5° C. The mixture is stirred an additional hour at 5° C. The mixture is diluted with 150 ml of water and the aqueous phase is separated.

The organic phase is diluted with 500 ml of dichloromethane, washed with 200 ml of water, and extracted with three 500 -ml portions of aqueous sodium hydroxide containing 45 g (1.1 moles) of sodium hydroxide. The three aqueous extracts, containing sodium 4-hydroxy-3-nitrobenzoate are combined.

A 500-ml portion of the extract containing approximately 0.33 mole of sodium 4-hydroxy-3-nitrobenzoate is sealed in a one-liter Hastelloy C autoclave with 5.0 g of 5 percent palladium-on-carbon. The reactor is purged with nitrogen and charged to 400 psig with hydrogen gas. The reactor is heated to 45° C. and maintained at 300 psig to 400 psig hydrogen pressure until hydrogen uptake is completed. The reactor is purged with nitrogen, the catalyst is filtered and the solution is acidified with 600 ml of 85 percent phosphoric acid. The solution is cooled to 0° C. and crude 3-amino-4-hydroxybenzoic acid hydrophosphate salt is filtered.

The crude salt is added to a mixture of 600 ml of 85 percent phosphoric acid, 1.0 g of $SnCl_2 2H_2O$ dissolved in 50 ml of 35 percent HCl, and 100 ml of water. The slurry is heated to 150° C. and water is added in sufficient quantity to dissolve all solid material. A 5 -g quantity of activated carbon is added and the solution is maintained at 150° C. for 10 minutes. The carbon is filtered, and the filtrate is cooled to 0° C. The resulting crystals are filtered, washed in cold n-propanol and dried under nitrogen gas. The recovered product contains 71 g (80 percent yield) of 3-amino-4-hydroxybenzoic acid hydrophosphate salt having one water of hydration.

EXAMPLE 2

Synthesis of AB-PBO Phosphate Monomer with Nickel Reduction

The process of Example 1 is repeated, except that the reduction is carried out using 2.5 g of nickel catalyst at a temperature of 95° C. The yield is approximately the same.

EXAMPLE 3

Polymerization of AB-PBO Monomer Phosphate Salt

Under nitrogen atmosphere, 15.0 g of AB-PBO monomer phosphate salt from Example 1 and 6.43 g of polyphosphoric acid containing 77 weight percent $P_2O_5$ are agitated at 95° C. for 1.3 hours. No foaming is observed. A 17.6 -g quantity of $P_2O_5$ is added, and agitation at 95° C. is continued for 4 hours. A 4.37 -g quantity of polyphosphoric acid is added, and stirring is continued at 95° C for 18 hours. The pressure is reduced to 160 Torr, and stirring at 95° C. is continued for 24 hours. The temperature is raised to 190° C. with stirring at 160 Torr for 24 hours.

The resulting dope is extruded according to known methods to form a fiber. AB-PBO polymer is coagulated from a sample of dope, washed with water, dried, ground, rewashed and redried. The polymer has an inherent viscosity of 14.5 dL/g in methanesulfonic acid at 25° C. and 0.0528 g/dL concentration.

What is claimed is:

1. A salt comprising AB-PBO monomer ions and phosphate ions wherein at least 99 percent of the organic content of the salt is AB-PBO monomer ions.

2. The salt of claim 1 wherein each AB-PBO monomer ion is an ion of an AB-PBO monomer containing: (1) a carbocyclic aromatic group having no more than about 18 carbon atoms, (2) an o-amino-basic moiety consisting of a primary amine group and a hydroxy group bonded to the aromatic group in ortho position with respect to each other, and (3) an electron-deficient carbon group bonded to the aromatic group.

3. The salt of claim 1 wherein the aromatic group in the AB-PBO monomer ion is a single six-membered ring or a plurality of unfused rings linked by a bond, an ether moiety, a sulfonyl moiety, or a halogenated alkyl moiety containing no more than about 6 carbon atoms.

4. The salt of claim 1 wherein the aromatic group in the AB-PBO monomer ion is contains no more than about 6 atoms.

5. The salt of claim 1 wherein the AB-PBO monomer ion is an ion of 3-hydroxy-4-aminobenzoic acid.

6. The salt of claim 1 wherein the AB-PBO monomer ion is an ion of 3-amino-4-hydroxybenzoic acid.

7. The salt of claim 6 wherein the phosphate ions are predominantly not condensed phosphate ions.

8. The salt of claim 6 wherein the average ratio of phosphate ions to AB-PBO monomer ions is about 1:1.

9. The salt of claim 6 wherein the purity of the salt, expressed as a weight percentage of the organic content which is AB-PBO monomer ion, is at least about 99.5 percent.

10. The salt of claim 6 wherein the purity of the salt, expressed as a weight percentage of the organic content which is AB-PBO monomer ion, is at least about 99.9 percent.

* * * * *

UNITED STATES PATENT AND TRADEMARK OFFICE
CERTIFICATE OF CORRECTION

PATENT NO. : 5,068,384

DATED : November 26, 1991

INVENTOR(S) : William J. Harris, Midland; Zenon Lysenko, Midland; and Carl W. Hurtig, Saginaw; all from Michigan It is certified that error appears in the above-identified patent and that said Letters Patent is hereby corrected as shown below:

Column 10, line 41, delete "about 6 atoms." Insert --about 6 carbon atoms.--

Signed and Sealed this

Twenty-seventh Day of April, 1993

*Attest:*

MICHAEL K. KIRK

*Attesting Officer*     Acting Commissioner of Patents and Trademarks

UNITED STATES PATENT AND TRADEMARK OFFICE
CERTIFICATE OF CORRECTION

PATENT NO. : 5,068,384

DATED : November 26, 1991

INVENTOR(S) : W. J. Harris, C. W. Hurtig, & Z. Lysenko

It is certified that error appears in the above-indentified patent and that said Letters Patent is hereby corrected as shown below:

Column 1, after the title, please insert
--STATEMENT OF GOVERNMENT INTEREST
     This invention was made with government support under Contract F33615-85-C-5113 awarded by the Department of the Air Force. The government has certain rights in this invention.--

Signed and Sealed this

Fifteenth Day of July, 1997

Attest:

BRUCE LEHMAN

Attesting Officer      Commissioner of Patents and Trademarks